US008844574B2

(12) United States Patent
Grob et al.

(10) Patent No.: US 8,844,574 B2
(45) Date of Patent: Sep. 30, 2014

(54) SPIRAL MIXER NOZZLE AND METHOD FOR MIXING TWO OR MORE FLUIDS AND PROCESS FOR MANUFACTURING ISOCYANATES

(75) Inventors: Neal Anthony Grob, Baton Rouge, LA (US); James LaVerne Allbright, Baton Rouge, LA (US)

(73) Assignee: Huntsman International LLC, The Woodlands, TX (US)

( * ) Notice: Subject to any disclaimer, the term of this patent is extended or adjusted under 35 U.S.C. 154(b) by 1254 days.

(21) Appl. No.: 11/910,945

(22) PCT Filed: Mar. 6, 2006

(86) PCT No.: PCT/EP2006/060488
§ 371 (c)(1),
(2), (4) Date: Feb. 11, 2010

(87) PCT Pub. No.: WO2006/108740
PCT Pub. Date: Oct. 19, 2006

(65) Prior Publication Data

US 2010/0130772 A1 May 27, 2010

Related U.S. Application Data

(60) Provisional application No. 60/669,545, filed on Apr. 8, 2005.

(51) Int. Cl.
*B01F 5/04* (2006.01)
*C07C 263/00* (2006.01)
*B01F 5/00* (2006.01)

(52) U.S. Cl.
CPC ............. *B01F 5/0403* (2013.01); *B01F 5/0077* (2013.01); *B01F 5/046* (2013.01)
USPC ........................................... 137/896; 560/347

(58) Field of Classification Search
None
See application file for complete search history.

(56) References Cited

U.S. PATENT DOCUMENTS

| | | | | |
|---|---|---|---|---|
| 4,925,101 | A * | 5/1990 | Konieczynski et al. | 239/8 |
| 5,788,667 | A * | 8/1998 | Stoller | 604/22 |
| 5,830,517 | A | 11/1998 | Clarke et al. | |
| 7,568,635 | B2 * | 8/2009 | Micheli | 239/263 |
| 7,851,648 | B2 * | 12/2010 | Sohn et al. | 560/347 |
| 2004/0008572 | A1 * | 1/2004 | Stuart | 366/162.4 |

FOREIGN PATENT DOCUMENTS

| | | | |
|---|---|---|---|
| DE | 103 33 922 A1 | | 2/2005 |
| FR | 2325637 | * | 5/1977 |
| SU | 1 498 545 | | 8/1989 |
| WO | WO 02/087736 | | 11/2002 |

* cited by examiner

*Primary Examiner* — Karl J Puttlitz
(74) *Attorney, Agent, or Firm* — Robert A. Diaz

(57) ABSTRACT

An apparatus for mixing at least first and second fluid, comprising: (a) a first nozzle comprising a first flow duct defining a first flow chamber, and having a first nozzle tip having a first discharge opening; and (b) a second nozzle comprising a second flow duct defining a second flow chamber, and having a second nozzle tip having a second discharge opening; wherein said first flow duct and said second flow duct are spirally wrapped each over the other. The invention also provides a process for mixing fluids, especially adapted for the production of isocyanates, and that is notably carried out in the apparatus of the invention.

9 Claims, 6 Drawing Sheets

SPIRAL MIXER NOZZLE AND METHOD FOR MIXING TWO OR MORE FLUIDS AND PROCESS FOR MANUFACTURING ISOCYANATES

CROSS REFERENCE TO RELATED APPLICATIONS

This application is the National Phase of International Application PCT/EP2006/060488, filed Mar. 6, 2006, which designated the U.S. and which claims priority to U.S. Pat. App. Ser. No. 60/669,545, filed Apr. 8, 2005. The noted applications are incorporated herein by reference.

This invention relates to a novel apparatus for mixing fluids, especially amine and phosgene, and to a process for mixing amine and phosgene in order to obtain carbamoyl chloride and isocyanate.

Many documents disclose nozzles for mixing fluids, especially reacting fluids. One particular example is found in the phosgenation reaction in which rapid mixing is a key parameter. Hence, many designs have been proposed for such nozzles, mostly with coaxial jets, which can be impinging or not.

However, there is still a need to further improve the mixing efficiency of the nozzles, especially in the phosgenation reaction.

An object of this invention is therefore to provide an apparatus for mixing at least first and second fluid, comprising (a) a first nozzle comprising a first flow duct defining a first flow chamber, and having a first nozzle tip having a first discharge opening; and (b) a second nozzle comprising a second flow duct defining a second flow chamber, and having a second nozzle tip having a second discharge opening;

wherein said first flow duct and said second flow duct are spirally wrapped each over the other;

wherein during operation of said apparatus, the first fluid flowing in the first flow chamber and exiting through the first discharge opening forms a first fluid jet, and the second fluid flowing in the second flow chamber forms at the second discharge opening a second fluid jet, said first and second fluid jets impinging upon each other, thereby mixing the first and second fluids.

The invention especially provides a substantially round apparatus for mixing at least first and second fluid, comprising: (a) a first nozzle comprising a first flow duct defining a first flow chamber, and having a first nozzle tip having a first discharge opening; and (b) a second nozzle comprising a second flow duct defining a second flow chamber, and having a second nozzle tip having a second discharge opening;

wherein said first flow duct and said second flow duct are spirally wrapped each over the other according to an Archimedean spiral having between 1 and 20 turns, and wherein said first and second nozzles are tapered;

wherein during operation of said apparatus, the first fluid flowing in the first flow chamber and exiting through the first discharge opening forms a first fluid jet, and the second fluid flowing in the second flow chamber forms at the second discharge opening a second fluid jet, said first and second fluid jets impinging upon each other, thereby mixing the first and second fluids.

Another object of this invention is also to provide a process for mixing at least first and second fluid, comprising the steps of: (a) forming a first fluid jet, consisting of the first fluid, at a first discharge position; (b) forming a second fluid jet, consisting of the second fluid, at a second discharge position; and (c) spirally wrapping each fluid jet over the other so that the said first and second fluid jets impinge upon each other, thereby mixing the first and second fluids.

The invention especially provides a process for mixing at least first and second fluid, comprising the steps of: (a) forming a first fluid jet, consisting of the first fluid, at a first discharge position; (b) forming a second fluid jet, consisting of the second fluid, at a second discharge position; and (c) spirally wrapping each fluid jet over the other according to an Archimedean spiral having between 1 and 20 turns so that the said first and second fluid jets impinge upon each other, thereby mixing the first and second fluids.

The process of the invention is especially useful for the production of isocyanates; the invention hence also provides a process for manufacturing isocyanates, comprising the mixing process of the invention as applied to amine and phosgene, followed by the step of reacting the mixed amine and phosgene. These processes are notably carried out in the apparatus of the invention.

Other objects, features and advantages will become more apparent after referring to the following specification. The invention is based on the use of a spiral-like nozzle, referred to hereinafter as a spiral nozzle. The specific geometry allows thin flows impinging on each other while at the same time having high mixing energy.

BRIEF DESCRIPTION OF THE DRAWINGS

Referring now to FIG. 1, there is shown a simple impinging coaxial jet mixer nozzle assembly 100 for mixing two fluids. Impinging coaxial jet mixer nozzle assembly 100 comprises inner flow duct 102 and an inner flow duct nozzle tip 104 disposed coaxially inside outer flow duct 101 and outer flow duct nozzle tip 105. Flow chamber 120 is defined as the space inside inner flow duct 102 and inner flow duct nozzle tip 104. Flow chamber 120 has two ends, supply end 130 and discharge end 110. Discharge end 110 of flow chamber 120 is formed by the discharge end of inner flow duct nozzle tip 104 and has a discharge opening of a given diameter. Flow chamber 121 begins as the annular space between outer flow duct 101 and inner flow duct 102. Flow chamber 121 continues as the annular space between outer flow duct nozzle tip 105 and inner flow duct 102. Flow chamber 121 continues further as the annular space between outer flow duct nozzle tip 105 and inner flow duct nozzle tip 104. Flow chamber 121 has two ends, supply end 131 and discharge end 132. Discharge end 132 of flow chamber 121 is formed by the discharge end of outer flow duct nozzle tip 105. Discharge end 110 of flow chamber 120 and discharge end 132 of flow chamber 121 are substantially proximate in the axial dimension. The first fluid flows through flow chamber 120 and is discharged at discharge end 110 as jet 103. The initial diameter of jet 103 is substantially equal to discharge opening diameter of nozzle tip 104. The second fluid flows through flow chamber 121 and is discharged at discharge end 132 as annular jet 106. The initial thickness of jet 106 is substantially equal to half of the difference between discharge opening diameter of nozzle tip 105 less the diameter of nozzle tip 104. The two coaxial jets 103 and 106 collide and mix as they exit nozzle tips 104 and 105 to form composite jet 107. The primary driving force for mixing is the kinetic energy and rate of turbulent energy dissipation of jets 103 and 106. The velocities of the fluids are selected by the relative designs of the nozzles 104 and 105. The angle at which nozzle tips 104 and 105 are tapered (i.e. the impingement angle) may vary, e.g. from 30 to 60°.

This device, while being known for many years still requires improvement in terms of mixing efficiency.

The nozzle assembly of the present invention thus provides an apparatus for mixing at least first and second fluids, the apparatus comprising first nozzle assembly means for forming a first spiral fluid jet 206, consisting of the first fluid, and second nozzle assembly means for forming a second spiral fluid jet 207 coaxial with and wrapped around said first spiral fluid jet 206, the second spiral fluid jet consisting of the second fluid, so that second spiral fluid jet 207 impinges upon first spiral fluid jet 206, thereby mixing the first and second fluids. This part will optionally be referred to as the nozzles sub-assembly 201.

It would be possible to provide further ducts for further fluids, if this is necessary.

Figure 2:
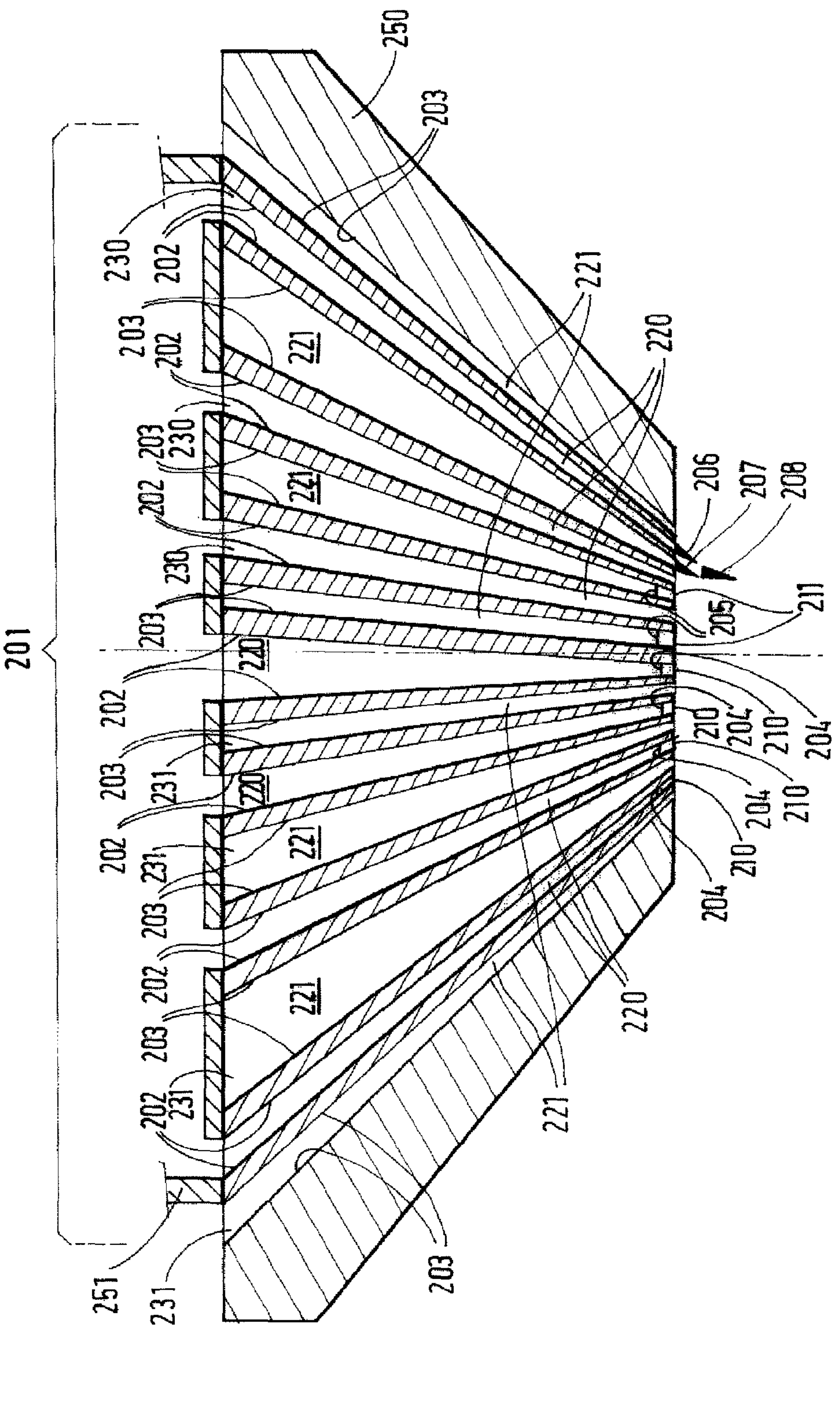
FIG. 2 is an axial, cross-sectional view of a nozzles sub-assembly of the invention.

Referring now to FIG. 2, there is shown an enlarged longitudinal cross section view of the nozzle assembly of the invention. The nozzles sub-assembly 201 is placed in a lower housing 250. The spirally wound assembly comprises first duct 2002 and second duct 203 arranged as follows. First flow chamber 220 is defined as the space inside first flow duct 202 and first flow duct nozzle tip 204 (only referenced on the left side of the drawing). First flow chamber 220 has two ends, supply end 230 (only referenced on the right side of the drawing) and discharge opening 210 (only referenced on the left side of the drawing). Discharge opening 210 of first flow chamber 220 is formed by the discharge end of first flow duct nozzle tip 204 and has a discharge gap of a given value. Second flow chamber 221 is defined as the space inside second flow duct 203 and second flow duct nozzle tip 205 (only referenced on the right side of the drawing). Second flow chamber 221 has two ends, supply end 231 (only referenced on the left side of the drawing) and discharge opening 211 (only referenced on the right side of the drawing). Supply end 231 is in the embodiment shown as a dead end, as the cover plate 251 will force the fluid to flow from the lateral entry (lumen of introduction). This will be further disclosed by reference to FIG. 3, FIG. 4 and FIG. 5. Discharge opening 211 of flow chamber 221 is formed by the discharge end of second flow duct nozzle tip 205 and has a discharge gap of a given value. One will notice that for the embodiment that is depicted, ducts 202 and 203 share common walls 241 and 242 (shown on FIG. 4), save for the outer turn where duct 203 is formed with the lower housing 250, which thus cooperates to form the spirally wound assembly. This assembly produces first and second jets 206 and 207, respectively, exiting at the first and second discharge openings, respectively. Jets 206 and 207 collide and mix as they exit nozzle tips 204 and 205 to form the composite jet 208. The most outer taper angle of the flow ducts may vary, e.g. from 30 to 60°, preferably 40 to 50° C., typically about 45° C. The taper angle of a given flow duct at a given point will be understood as the angle between the axis of the assembly and the general direction of flow at the exit of the given duct at the given point, prior to impinging. It will be understood that the flow duct will have a taper angle that will vary along the circular path of the flow duct. Especially, the taper angle may increase from the center to the outer of the apparatus. It will also be noted that the inner taper angle of the flow duct may also vary from 0 to 45°, preferably from 0 to 15°.

In the embodiment as shown, one will notice that said first flow chamber 220 has dimensions substantially decreasing along the first flow duct towards the first discharge opening. The ratio (gap of supply end 230) to (gap of discharge opening 210) may vary from 1 to 10, preferably 2 to 4.

In the embodiment as shown, one will notice that said second flow chamber 221 has also dimensions substantially decreasing along the second flow duct towards the second discharge opening.

In the embodiment as shown (as will be further indicated on FIG. 4), one will notice that said second flow chamber 221 has also dimensions substantially decreasing from the outer to the inner of the spirally wrapped ducts. The ratio (gap of outer end) to (gap of inner end) may also vary at the supply level or the discharge level or both.

Here the various dimensions of the respective discharge openings (i.e. width or gap) are chosen so as to impart the required velocities. Typically, the (superficial) velocity of the jet 206 will be 5-90 ft/sec, preferably 20-70 ft/sec. Typically, the (superficial) velocity of the jet 207 will be 5-70 ft/sec, preferably 10-40 ft/sec. The gap at nozzle tip 204 is typically 0.04"-0.20", preferably 0.05"-0.10". The gap at nozzle tip 205 is 0.04"-0.20", preferably 0.05"-0.10". These gaps may be constant or may be varied along the spiral. The wall thickness, or separating gap, is generally less than each of the gap for the discharges openings and will typically be 0.03"-0.10", preferably 0.03"-0.06". If one considers each discharge opening, one may measure an approximate length for the discharge (considered as a deployed line). The discharge openings have typically a length L such that the ratio L on gap is from 20 to 200, preferably 60 to 150. The discharge gap 210 can be smaller, equal or larger than the discharge gap 211. The discharge gap 211 can also vary from the outer to the inner, and e.g. 211 on outer is half 211 on inner. The discharge gap 210 can also vary the same way, if need be.

Figure 3:
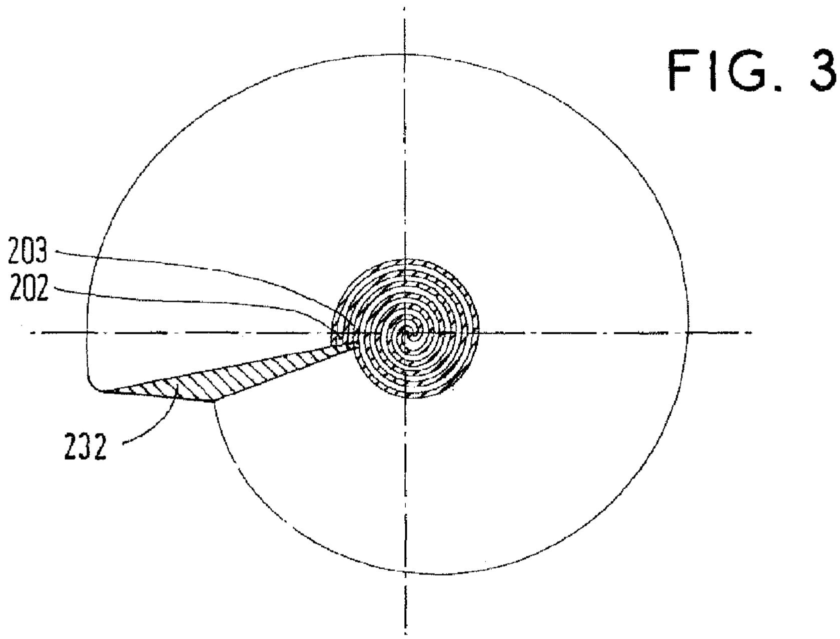
FIG. 3 is a bottom enlarged view of a nozzles sub-assembly of the invention.

Referring now to FIG. 3, there is shown an enlarged bottom view of the nozzles sub-assembly of the first embodiment of the invention, without the lower housing. One may notice ducts 202 and 203 sharing common walls, where duct 202 is the one resulting from the loop-like turn while duct 203 results from the wrapping (and ultimately from the encasing into the lower housing). The lumen of introduction is identified as 232 on the drawing.

Figure 4:
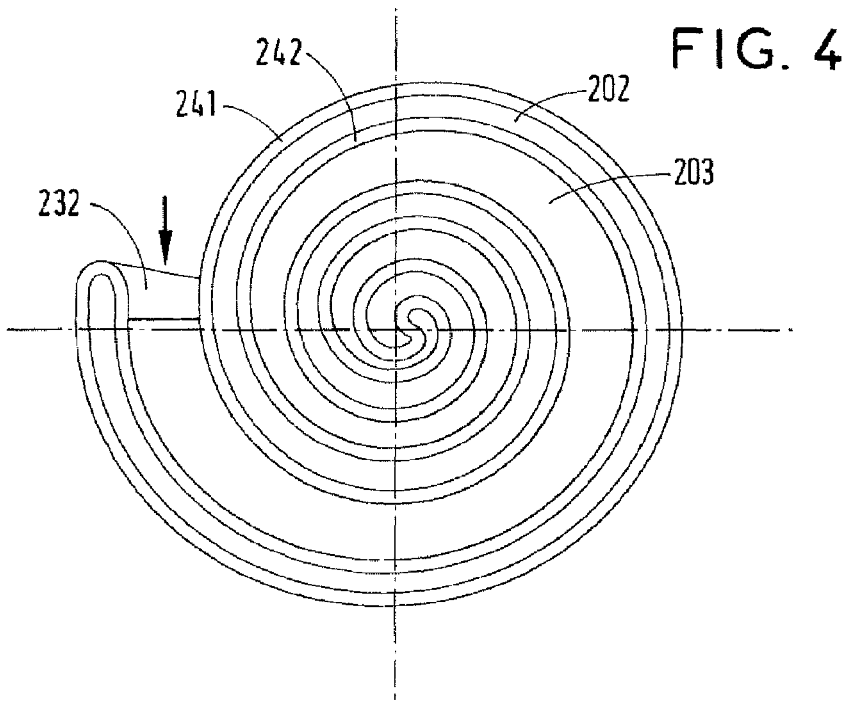
FIG. 4 is a top enlarged view of a nozzles sub-assembly of the invention.

Referring now to FIG. 4, there is shown an enlarged top view of the nozzles sub-assembly of the first embodiment of the invention, without the lower housing. On FIG. 4 one can see walls 241 and 242, as well as the lumen for introduction of the second fluid 232, where the arrow represents the general injection direction of the flow in second duct 203. This will be further disclosed in reference to FIG. 5.

Figure 5:
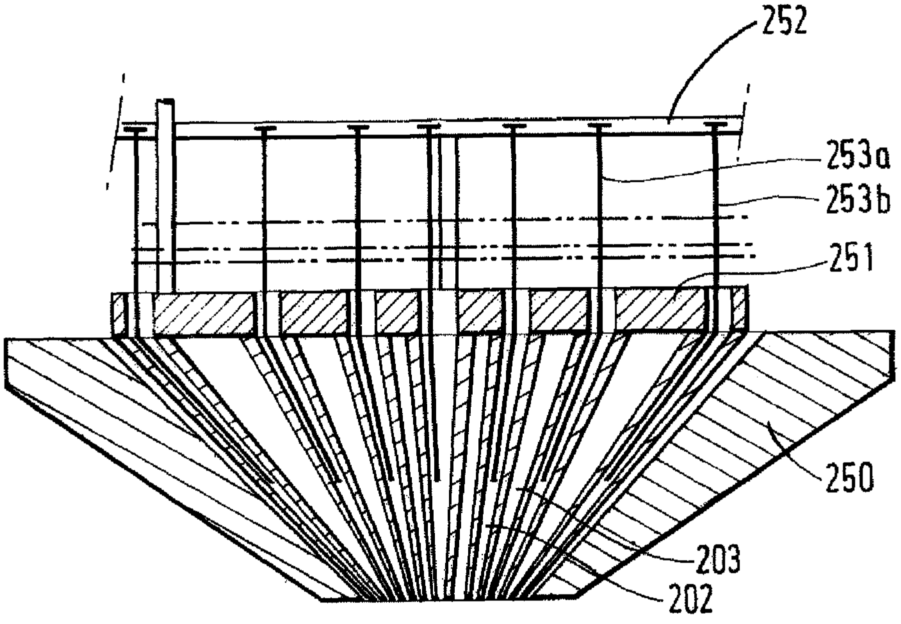
FIG. 5 is an axial, cross-sectional view of a nozzle of the invention.

Referring now to FIG. 5, there is shown an enlarged longitudinal cross section view of the spirally wound assembly of the invention. The first and second ducts 202 and 203 are still represented, as well as the lower housing 250. One can notice on FIG. 5 a second fluid cover 251 for introduction of the second fluid. Since the cover is placed on top of the second duct 203 which results from the wrapping (and ultimately from the encasing into the lower housing), the cover 251 will also, in the embodiment shown, have a form that is generally wound. When fed into the second duct 203 from the lumen of introduction 232, the second fluid will then flow according to a direction (identified on FIG. 4 by the arrow) that will be substantially tangential to the axis of the nozzle. By using a tangential feed for the second fluid, there is an extra benefit in achieving a tangential velocity vector, resulting in a swirling effect and ultimately in enhanced mixing. 253*a* and 253*b* are tines.

As can be derived from the preceding drawings, the nozzle assembly of the invention is spirally wound or wrapped on itself. The term "ducts spirally wrapped each over the other" is intended to cover those cases where one duct will wrap the other over more than one turn. It will be generally considered, for the purpose of the instant invention, that a curve will form a turn if there exits a straight line that intersects said curve in at least 3 different locations. One may count the number of turns by counting the number of intersections of said straight line with the curve. One way of expressing this is to count the number of intersections as 2n+1, where n is the number of turns. Spiral is here intended to cover any substantially continuous curve drawn at ever increasing distance from fixed point. Wrapped is here to denote that there is more than one turn, resulting in an overlap of ducts. The "turn" need not necessarily mean round, although this is the preferred embodiment, and this covers also spiral-like squared wrapped ducts. Asymmetry resulting from this design enhances mixing of the two fluids. The number of turns is not critical, and may vary between broad limits such as between 1 and 20 turns. In one embodiment, this number is quite high, for example for the first embodiment depicted, which may be depicted as the "tight spiral" embodiment. The number of turns may vary here between 3 and 10. In another embodiment, this number is quite low, and may be depicted as the "open spiral" embodiment. The number of turns may vary then between 1.05 and 1.5. The case where double ducts are wrapped is also foreseen. The first and second flow ducts are preferably spirally wrapped each over the other according to an Archimedean spiral, and more preferably according to an Archimedes' spiral. An Archimedean spiral is a spiral with polar equation $r=a\theta^{1/\gamma}$, where r is the radial distance, θ is the polar angle, and y is a constant which determines how tightly the spiral is "wrapped". An Archimedes' spiral is the spiral for which y is one.

Figure 6:
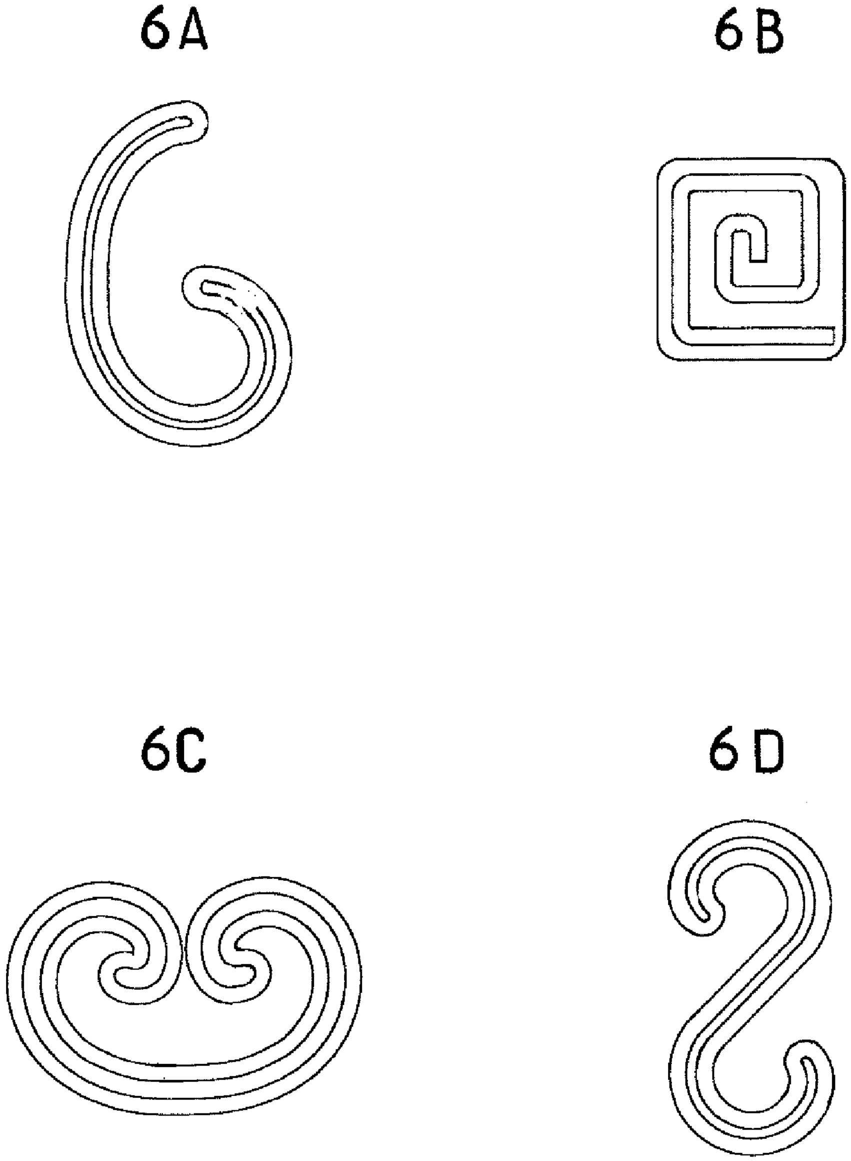
FIGS. 6A, 6B, 6C and 6D are further embodiments of the invention.

FIG. 6 shows other embodiments of the invention. FIG. 6A represents the "open spiral" embodiment. FIG. 6B represents the "square spiral" embodiment. FIG. 6C represents a "heart spiral" embodiment. FIG. 6D represents a "sigmoid spiral" embodiment. FIG. 5 shows another embodiment of the invention, comprising a cleaning device. In this embodiment, a carriage 252, mounted co-axially along the nozzle, is provided with tines 243*a*, 243*b*, 243*c*, etc. The tines are located in one of the ducts, here the first duct 202. When the carriage 252 is displaced along the axis of nozzle using proper mechanical means (not shown), the tines will scrape debris and deposits lodged in the first duct 202. An unplugged nozzle assembly can thus be obtained without having to shut down the process to remove the plugged or restricted flow nozzle assembly.

Figure 1:
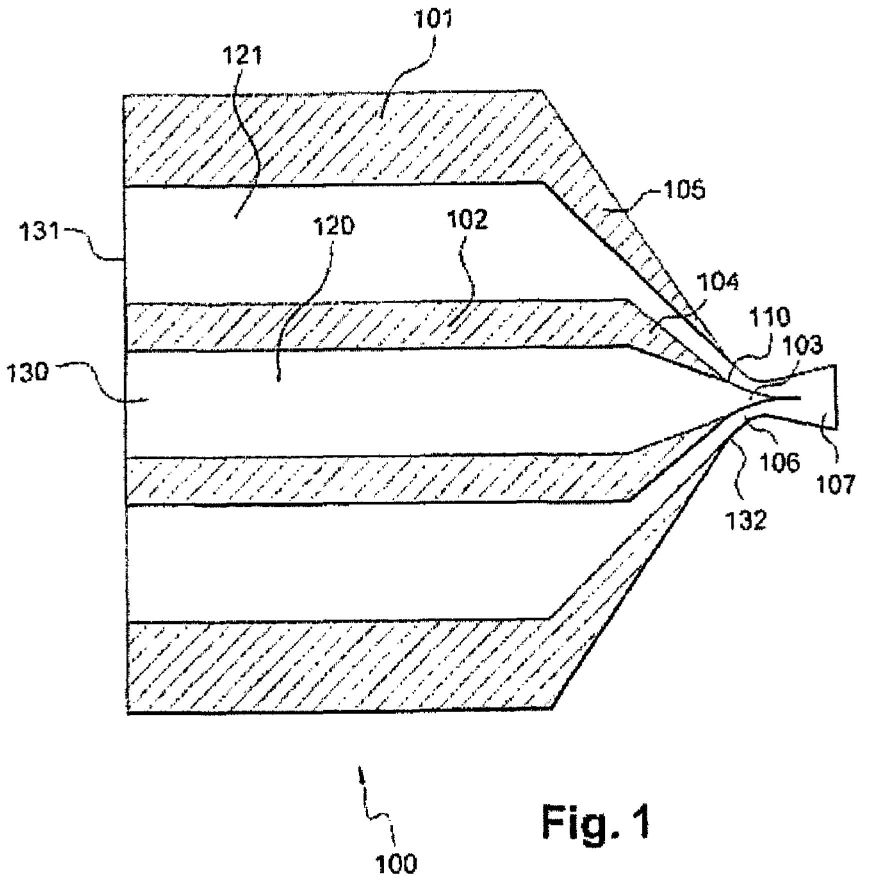
FIG. 1 is an axial, cross-sectional view of a conventional simple coaxial jet mixer nozzle assembly.
Figure 7:
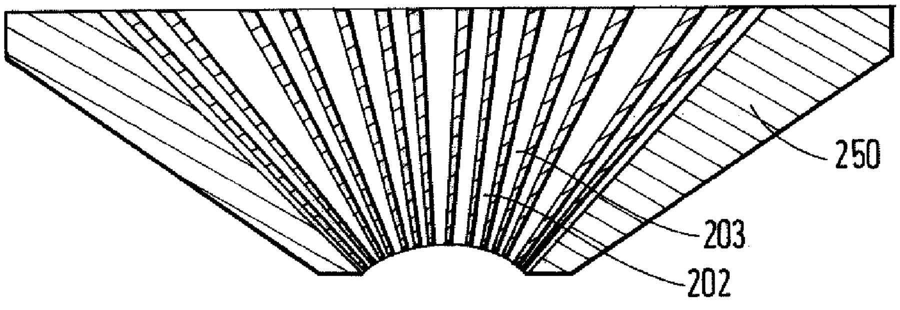
FIG. 7 is an axial, cross-sectional view of further embodiment of a nozzles sub-assembly of the invention.

FIG. 7 shows another embodiment of the invention, which corresponds to the one of FIG. 1, in which the bottom part of the nozzles sub-assembly has been modified in a curved shape. This may be represented as the suppression of a part corresponding to a portion of a sphere (or any other rounded form).

The surfaces of the nozzle assembly of the invention can also be treated and/or finished with conventional surface treatments including coatings, polishing, adding ridges or grooves, if need be.

The invention provides several advantages over prior art nozzle assemblies. One advantage is a substantial gain in mixing efficiency, compared to prior nozzle assemblies. The specific geometry of the nozzle does not require impingement on other surfaces, and this avoids erosion and expensive alignment. The present invention may also provide for adjustment of the nozzles sub-assembly 201 (including the cover plate 251 and associated carriages, if any) with respect to the lower housing 250. Axial movement of nozzles sub-assembly 201 with relation to lower housing 250 is achieved by mechanical means (not shown) for adjustment of the axial position of sub-assembly 201. These mechanical means may typically comprise a shaft on which the sub-assembly is mounted and means for displacement of this shaft. By adjusting the sub-assembly with respect to the lower housing, one may then vary the dimensions of the outer duct 203 proximate the lower housing 250 and thus the flow rate through this duct. This will provides adjustment means for the reaction that will take place. An advantage of the embodiment with movable sub-assembly is the on-line adjustability of the cross-sectional area for flow of the extreme outer jet. On-line adjustability denotes the ability to make adjustments without undue interference with an ongoing process. In commercial scale processes, on-line adjustability allows for frequent adjustment of the nozzles for, e.g., maximum pressure drop or flow rate at the extreme outer discharge point of the nozzle. Another advantage is improved turn-down capability of commercial processes. The adjustability may allow a wider range of operating rates for some processes. Another advantage is the ability to stroke sub-assembly relative to lower housing 250 through its full travel path with the nozzle assembly installed. Commercial scale mixer assemblies can become plugged with debris or solid deposits. Stroking sub-assembly 201 on lower housing 250 can scrape debris and deposits lodged in extreme outer duct, in case no tine is present at this duct location.

The nozzle assembly is simple to manufacture and install, where one process for its manufacture is electrical wire discharge machining, which is a technology widely available. A process for manufacturing the nozzles sub-assembly of the apparatus of the invention will typically comprise the steps of (a) providing a preform; and (b) wire electrical discharge machining said preform. The housing may be manufactured using conventional machining. One further advantage is that there are no continuously moving or rotating parts, avoiding thus any mechanical wear of the system.

The invention is especially useful for very fast chemical reactions where fast mixing is crucial. Hence, the invention is useful as a pre-phosgenation reactor for the preparation of isocyanates. In this embodiment, the fluid flowing through the inner path is a primary amine, optionally dissolved in a solvent. In this embodiment, the fluid flowing through the outer path is phosgene, optionally dissolved in a solvent. Hence, the invention is useful for the manufacture of various isocyanates, and may e.g. be selected from aromatic, aliphatic, cycloaliphatic and araliphatic polyisocyanates.

The nozzle assembly allows for minimizing the excess phosgene used in the reaction, or having higher blend strength or higher output. Blend strength refers to the concentration of amine within the solvent and amine mixture that comprises the amine feed to the nozzle.

It is possible, as in the known techniques, to recycle a solution of solvent, phosgene, and isocyanate singly or in combination back into the phosgene flow. In one embodiment, it is preferred not to recycle this solution.

In particular are produced the aromatic polyisocyanates such as methylene diphenyl diisocyanate (MDI) (e.g. in the form of its 2,4'-, 2,2'- and 4,4'-isomers and mixtures thereof), and mixtures of methylene diphenyl diisocyanates (MDI) and oligomers thereof known in the art as "crude" or polymeric MDI (polymethylene polyphenylene polyisocyanates) having an isocyanate functionality of greater than 2, toluene diisocyanate (TDI) (e.g. in the form of its 2,4- and 2,6-isomers and mixtures thereof), 2,5-naphthalene diisocyanate and 1,4-diisocyanatobenzene (PPDI). Other organic polyisocyanates which may be obtained include the aliphatic diisocyanates such as isophorone diisocyanate (IPDI), 1,6-diisocyanatohexane and 4,4'-diisocyanatodicyclo-hexylmethane (HMDI). Still other isocyanates that can be produced are xylene diisocyanates, phenyl isocyanates.

If need be, the geometry of the nozzle assembly of the invention can be adapted to the specific isocyanate to be manufactured. Routine tests will enable one skilled in the art to define the optimum values for the gaps and lengths, as well as operative conditions.

The nozzle assembly of the invention can be used in a classical continuously stirred tank reactor (with or without baffles).

The nozzle assembly can be in the vapor space or submerged. The nozzle assembly of the invention can be used in all existing equipment with minimal adaptation, thus saving costs. Also, the nozzle assembly of the invention can be used in any type of reactor; for example the nozzle assembly can be mounted at the bottom of a rotary reactor equipped with impellers and baffles or the nozzle assembly can be used as an injection device in a rotor/stator type reactor.

The process conditions are those typically used. The phosgene:amine molar ratio is generally in excess and ranges from 1.1:1 to 10:1, preferably from 1.3:1 to 5:1. A solvent is generally used for the amine and the phosgene. Exemplary solvents are chlorinated aryl and alkylaryl such as monchlorobenzene (MCB), o- and p-dichlorobenzene, trichlorobenzene and the corresponding toluene, xylene, methylbenzene, naphthalene, and many others known in the art such as toluene, xylenes, nitrobenzene, ketones, and esters. The amine blend strength can be from 5 to 40 wt % while the phosgene concentration can be from 40 to 100 wt %. The temperature of the amine flow is generally comprised from 40 to 80° C. while the temperature of the phosgene flow is generally comprised from −20 to 0° C. The process is conducted at a pressure (at the mixing zone) generally from atmospheric to 100 psig.

It is also possible to use one or more further reactors (esp. CSTRs) to complete the reaction. In the process for manufacturing isocyanates, it is also possible to use typical units for recycling solvent and/or excess phosgene, for removing HCl and recycling HCl to chlorine, etc.

The depicted and described preferred embodiments of the invention are exemplary only and are not exhaustive of the scope of the invention.

The invention claimed is:

1. A process for mixing at least a first and second fluid, wherein said first and second fluid having a different composition, comprising:

forming a first fluid jet from the first fluid at a first discharge opening of a first nozzle wherein the first nozzle comprises a first flow duct defining a first flow chamber and a first nozzle tip wherein the first nozzle tip comprises the first discharge opening;

forming a second fluid jet from the second fluid at a second discharge opening of a second nozzle wherein the second nozzle comprises a second flow duct defining a second flow chamber; and a second nozzle tip wherein the second nozzle tip comprises the second discharge opening;

wherein the first and second discharge openings are spirally wrapped over the other about a central axis; and impinging the first fluid jet that exits the first discharge opening with the second fluid jet that exits the second discharge opening thereby mixing the first and second fluids and obtaining a blend of said first and second fluid.

2. The process of claim 1, wherein spirally wrapping each fluid jet includes spirally wrapping according to an Archimedean spiral.

3. The process of claim 1, wherein spirally wrapping each fluid jet includes forming between 1 and 20 turns.

4. The process of claim 1, including swirling said first fluid jet and said second fluid jet.

5. The process of claim 1, including mixing the first fluid and the second fluid, one of the first and second fluid being an amine, the other of the first and second fluid being phosgene.

6. The process of claim 5, including reacting the mixed amine and phosgene to manufacture an isocyanate.

7. The process of claim 6, wherein manufacturing an isocyanate includes manufacturing one or more isocyanates selected from the group consisting of methylene diphenyl diisocyanate and polymeric variants thereof, toluene diisocyanate 1,5-naphthalene diisocyanate, 1,4-diisocyanatobenzene, xylene diisocyanate, phenyl isocyanate, isophorone diisocyanate, 1,6-diisocyanatohexane and 4,4'-diisocyanatodicyclo-hexylmethane.

8. The process of claim 1, wherein the first and second flow ducts are tapered.

9. The process of claim 8, wherein the taper comprises a tapering angle and the tapering angle increases from the central axis to an outer axis.

* * * * *